United States Patent [19]

Hodgson

[11] 4,316,182
[45] Feb. 16, 1982

[54] VENTILATOR DISCONNECTION ALARM

[76] Inventor: William R. Hodgson, 36 Ashley St., Chatswood, New South Wales, Australia

[21] Appl. No.: 125,766

[22] Filed: Feb. 27, 1980

[30] Foreign Application Priority Data

Feb. 28, 1979 [AU] Australia .................. PD7858

[51] Int. Cl.³ .................. G08B 21/00; A61M 16/00
[52] U.S. Cl. .................. 340/606; 128/204.21; 128/204.23; 128/205.23
[58] Field of Search .................. 340/605, 606; 137/557, 137/312; 128/202.22, 204.24, 205.17, 205.23, 207.15, 204.21, 204.23

[56] References Cited

U.S. PATENT DOCUMENTS 3,566,387 2/1971 Schoener et al. .......... 128/204.23 X
4,155,357 5/1979 Dahl .............................. 128/202.22

Primary Examiner—John W. Caldwell, Sr.
Assistant Examiner—Daniel Myer
Attorney, Agent, or Firm—Steinberg & Raskin

[57] ABSTRACT

A control and actuating circuit includes a switch operated by each breath delivered by a ventilator to a patient connected to the ventilator. The circuit is connected to an alarm, maintains the alarm inoperable, and places the alarm in operable condition upon operation of the switch due to the first breath delivered to the patient. The alarm is thence capable of operation if breaths additional to the first breath fail to occur.

6 Claims, 6 Drawing Figures

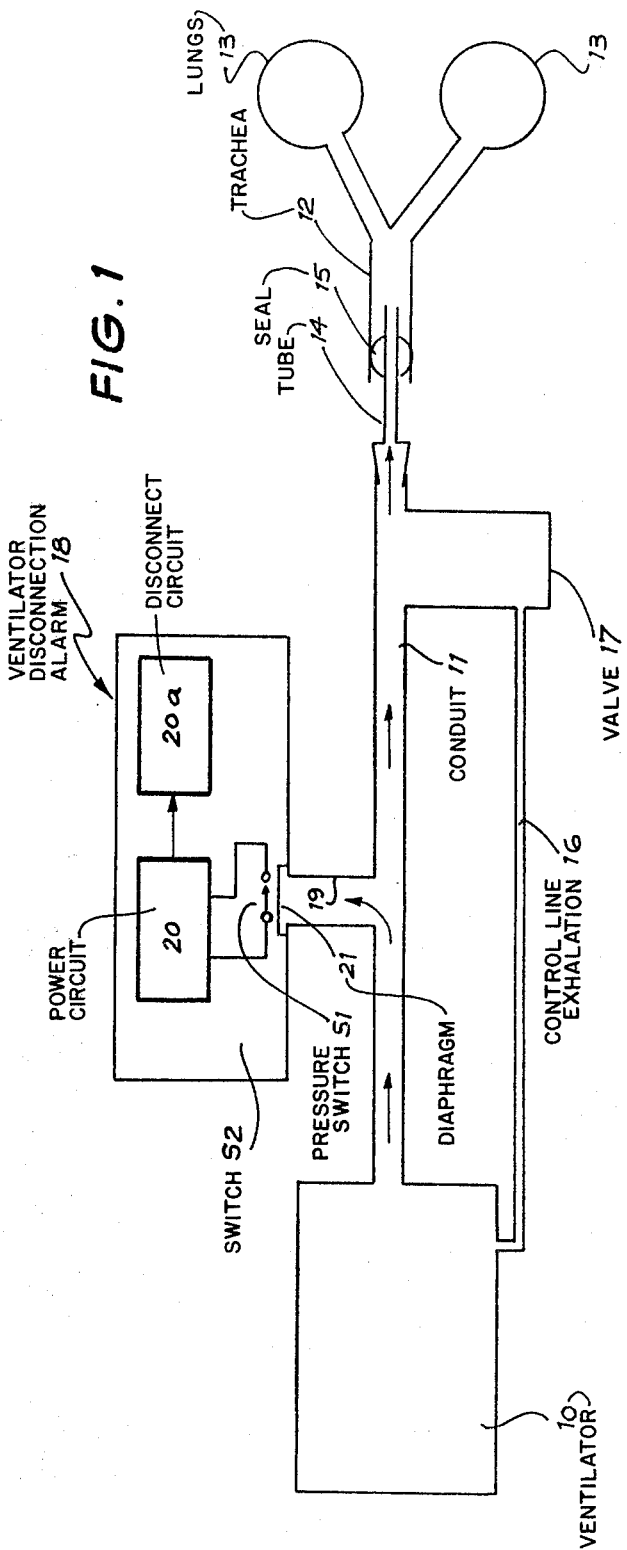

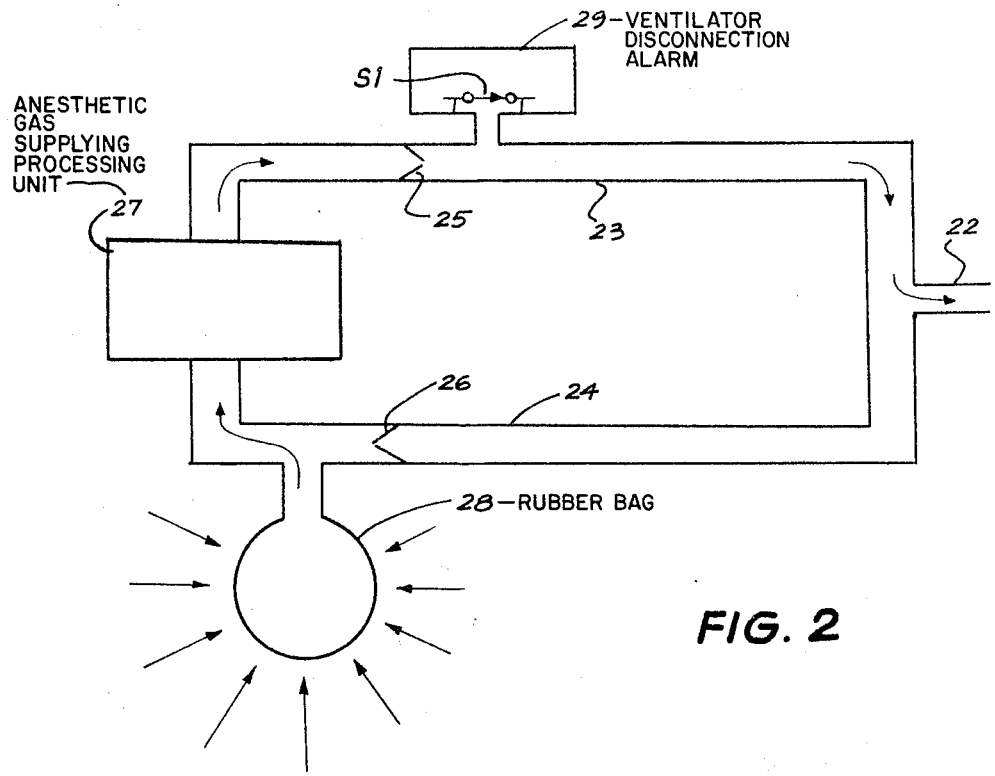
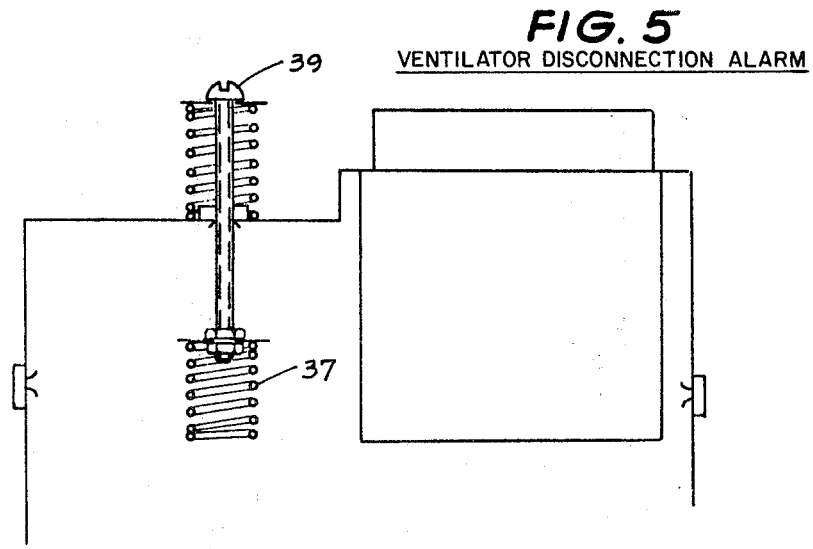

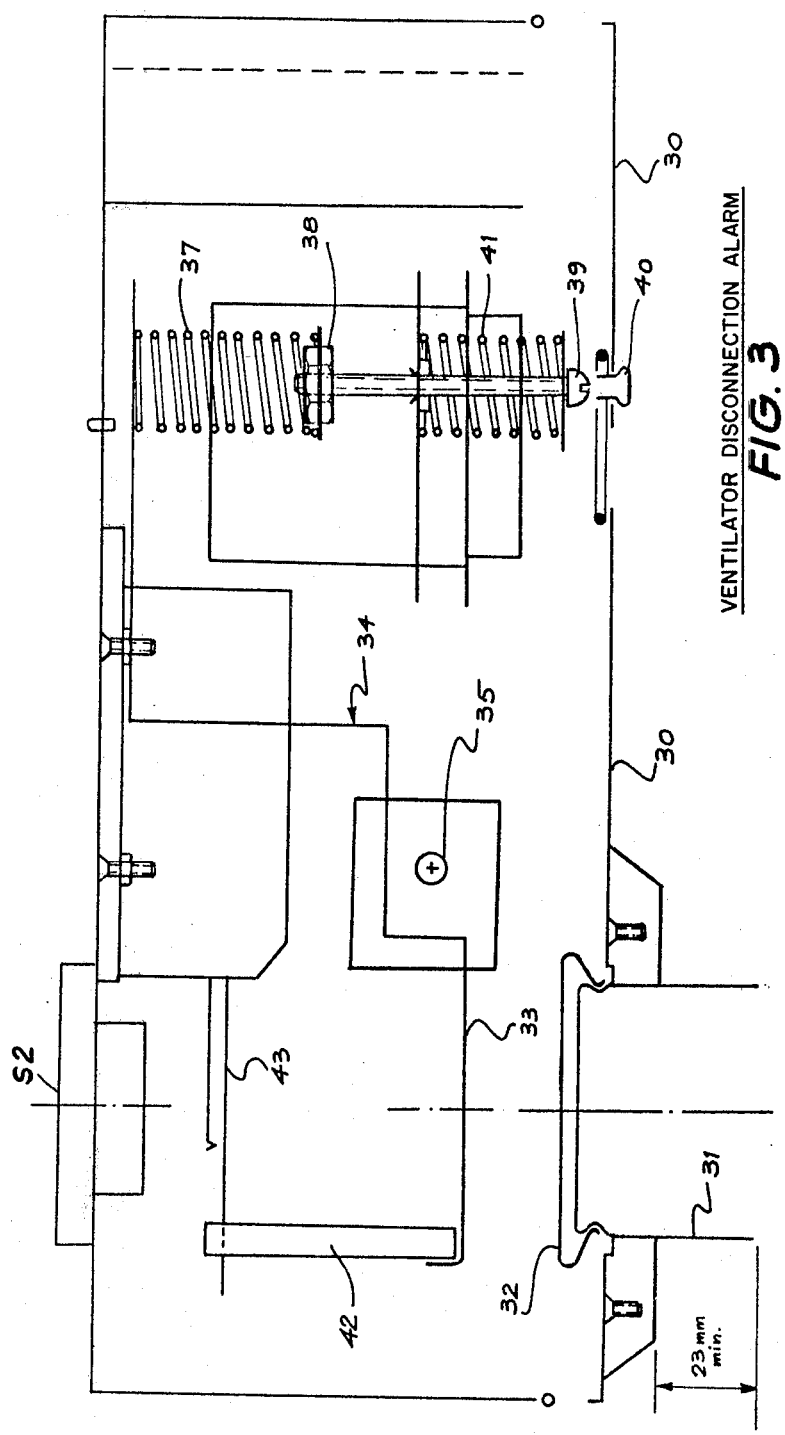

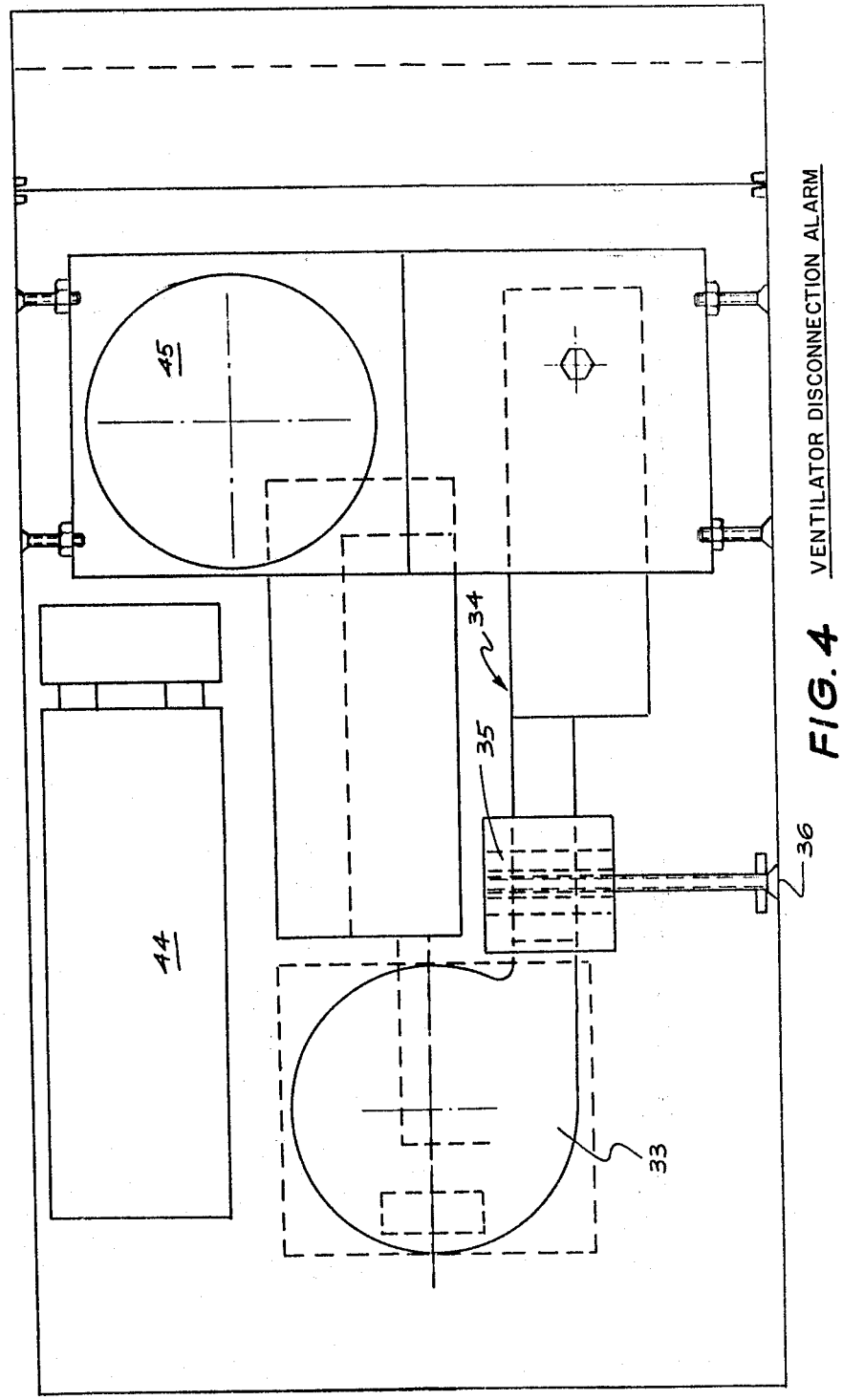

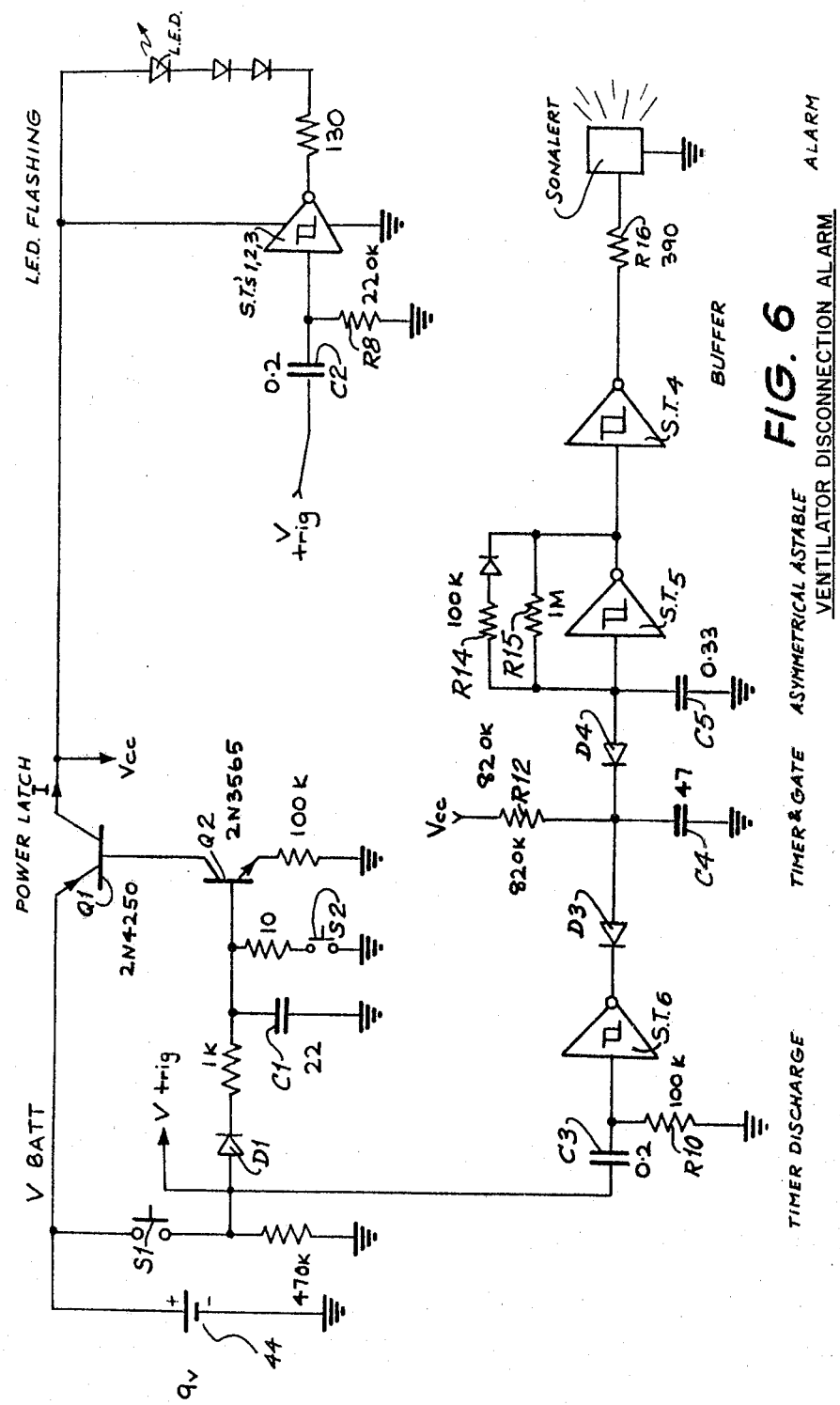

VENTILATOR DISCONNECTION ALARM

BACKGROUND OF THE INVENTION

The present invention relates to a ventilator disconnection alarm for use in connection with ventilators such as are used in the practice of medicine to supply air or other gas to a patient incapable of normal breathing.

When a person is paralyzed either by disease or by drugs his life becomes dependent on some form of artificial breathing (called "ventilation") as his own muscles are no longer capable of moving air in and out of his lungs. Generally the breathing machine or "ventilator" is connected to a tube sealed in the patient's trachea and blows gas under positive pressure into the lungs at appropriate intervals. When the inward breath stops the breathing out process is accomplished by the natural collapsing tendency of the lungs independent of muscles or machinery.

As the consequences of prolonged failure of the ventilator or accidental disconnection of the associated tubing are fatal, devices to detect and notify such events are in common use. Powered either by mains or battery these alarms generally detect the rise in back pressure associated with the lung's natural collapsing forces which increase as the lungs fill. If no such pressure rise occurs within a predetermined time an alarm is sounded. Occasionally, without changing the basic principle an alternate event, (such as varying temperature, expiratory flow, or measured expired gas volume) is chosen to detect each breath.

When temporary interference with the breathing equipment is planned or when artificial ventilation is no longer required the alarm is turned off. If, therefore, when ventilation is re-established or another patient connected to the equipment, the attendant is preoccupied, forgetful, or careless in turning the alarm back on all protection is lost. Some existing devices provide a warning "beep" when temporarily disabled. This warning is not available, however, when power is permanently removed during periods of disuse. Other alarms incorporate a "time-disable" feature whereby the period of disablement is limited to 60 seconds or less. Again such an alarm must be completely shut off when the ventilator is not in use. To eliminate this potential loss of protection against a fatal accident, the present invention provides a new solution.

SUMMARY OF THE INVENTION

The solution provided according to the present invention is to make use of the effect on the patient of the first breath delivered to him to activate the alarm in preparation for detection of ventilation failure. In preferred forms of the invention a passive pressure-sensitive switch is connected to the patient gas circuit and detects the pressure excursions representing the filling and emptying of the lungs as in many traditional alarms. In such preferred forms of the present invention this switch not only notifies the "breath-detecting" circuit that a breath has occurred but also turns on the power to the alarm itself. Since the passive switch consumes no power it can always remain operational. There is no longer a need to remember to turn on the alarm as the first filling of the lungs closes the switch and turns on the alarm in readiness for detection of a 20 second period in which the switch does not re-close. When interruption of the ventilation is intended the power is removed by operation of another switch on the panel of the instrument. The next breath, however, immediately puts the alarm back in operation.

The present invention consists in a ventilator disconnection alarm consisting of warning means for producing an audible warning, a power supply device, a switch operated by the occurrence of each breath delivered to a patient connected to said ventilator, said switch being connected to circuit means arranged to initiate operation of said warning means unless operation of said switch due to the occurrence of a breath occurs at predetermined short intervals of time, for example 20 seconds after each operation, said switch being further connected to "alarm-permitting" circuitry in such fashion that operation of the switch causes the "alarm-permitting" circuitry to enter a mode such that actuating power is allowed to pass to said warning means, and additional manually operable switch means connected to said "alarm-permitting" circuitry such that momentary operation of said manually operable switch means cause the "alarm-permitting" circuitry to leave said mode whereby actuating power is not allowed to pass to said warning means.

It is preferred that said power supply device is an electrical power supply device, that said circuit means is electric circuit means and that said switch is an electric switch. It is however the case that other means for controlling the alarm may be used such as, for example, fluidic logic circuitry using an appropriate power source.

BRIEF DESCRIPTION OF THE DRAWINGS

In order that the nature of the invention may be better understood preferred embodiments thereof are hereinafter described, by way of example, with reference to the accompanying drawings in which:

FIG. 1 illustrates diagrammatically the use of a ventilator alarm according to the invention in an intensive care unit, FIG. 2 illustrates diagrammatically the operation of an anesthetic machine incorporating the invention, FIG. 3 is a side view of a ventilator alarm according to the invention, FIG. 4 is a bottom view of the alarm shown in FIG. 3, FIG. 5 is an end view thereof, and FIG. 6 is a circuit diagram of the alarm.

DESCRIPTION OF PREFERRED EMBODIMENT

There are two situations in which a ventilator disconnection alarm requirement arises, in intensive care units and in the administration of anesthetics.

FIG. 1 illustrates in a purely diagrammatic manner the situation in an intensive care unit. In this a ventilator 10 is connected through the conduit 11 to the trachea 12 of a patient which communicates with his lungs 13. A tube 14 projects from the conduit 11 into the trachea 12 and is sealed with it by means of the seal 15. The ventilator 10 is connected by means of a control line 16 to an exhalation valve 17 through which air exhaled by the patient passes out of the system.

The conduit 11 is connected to the ventilator disconnection alarm indicated generally at 18 by the tube 19. The alarm 18 which is described in detail below consists of a power circuit 20 connected to a disconnect circuit 20a. With the power circuit 20 is associated the pressure switch S1. As will be explained in more detail below, this switch is normally off but is moved to the on position by a rise in pressure in the passage 19, the switch being operated by displacement of the diaphragm 21 under pressure.

In intensive care units the patient generally is not breathing at the outset. He is connected to a ventilator as in FIG. 1, and the first few breaths are delivered under extremely close observation as the ventilator controls are adjusted to suit the individual. The first breath, therefore, which is certain to be carefully observed and hence certain to occur, is used to turn on the alarm power. The first breath acts to close the switch S1 which has the effect of supplying power to the alarm 18 to bring it into a state of readiness. It is to be noted that this occurs quite automatically on the occurrence of the first breath. Provided that the alarm is properly equipped with a battery there is no possibility of an operator forgetting to put it into a state of readiness. Subsequent breaths alternate between inspiration during which air is supplied by the ventilator to the patient's lungs and expiration during which air passes out of the exhalation valve 17. During expiration pressure in the conduit 11 will fall and the switch S1 will revert to its normally open position. During the next inspiration pressure will rise again and the switch will close. So long as a closure of the switch occurs every 15 to 20 seconds no alarm will be given. If however the switch opens during expiration and no closure occurs within that period an alarm will be sounded. This could happen if a disconnection of the ventilator to the patient occurred, for example, at the seal 15 with the trachea 12. The alarm may be stopped either by reinstituting effective ventilation, hence closing the switch S1 or by removing power from the alarm circuits by operation of switch S2 which functions as described below.

In the operating room the situation is somewhat different from that in an intensive care unit. FIG. 2 illustrates diagrammatically the apparatus used. A patient (not shown) is connected at the point 22 to a conduit system including an upper conduit 23 and a lower conduit 24 which have in them respectively one-way valves 25 and 26. These are connected to a processing unit 27 by means of which the anesthetic gas is supplied. The lower conduit 24 also includes a compressible rubber bag 28. A ventilator disconnection alarm 29 is arranged in the conduit 23 and this includes the switch S2 referred to above. Having received the paralyzing drug the unconscious patient's breathing gradually fails. Anticipating this the anesthetist initially assists the breathing and finally is required to provide all the ventilation which he does by squeezing the collapsible rubber bag 28.

While the patient is breathing the circuit pressure is essentially atmospheric, the bag expanding and collapsing to keep it so. When the anesthetist squeezes the bag, pressure rises above atmospheric as gas is forced into the patient's lungs. This pressure rise closes the switch S2 in the alarm 29 which is activated in the manner described above. If subsequently the manual squeezing ceases the alarm will sound. In some cases the bag 28 may be replaced by means of a mechanical ventilator in which case the system will function substantially as described in connection with FIG. 1. The important feature of the whole arrangement is that the alarm is placed in an operational condition by the first rise in pressure in the system and there is thus no possibility of forgetting to activate it.

A preferred form of the alarm according to the invention is shown in FIGS. 3, 4 and 5.

The device is enclosed in a two piece case and sealed to prevent ingress of "splashed" water. The bottom cover 30 (or base) of the case is penetrated by a tubing 31 of 22 mm outside/15 mm inside standard taper diameters (in accordance with Standards Association of Australia Standard As-T37). This tubing 31 provides both mechanical support and gas connection to the patient circuit. Over the inside end of the tubing is stretched a thin silastic dome or "top-hat" 32 which is free to move along the extended axis of the tubing 31 in response to fluid pressure within. As no other working parts are permanently fixed to the base plate 30 and patient gases are not able to pass the dome 32 the entire assembly which could become infected can be removed and sterilized.

As the dome 32 moves outward from the tubing 31 it deflects a metal disc diaphragm 33 an extension of a pivot arm 34, the supporting brass sleeve 35 of which is free to rotate around a brass machine screw 36 penetrating the side wall of the main case. At the opposite end of the pivot arm 34 a reaction spring 37 is compressed between the pivot arm 34 and a moveable support 38 which can be screw-adjusted by the screw 39 to alter the spring force and hence make the input pressure required to cause a switch-closing deflection of the diaphragm approximately 11–14 cm $H_2O$.

The end of the screw 39 is accessible through a hole in the base plate 30 which is sealed by the plug 40. An antivibration locking spring 41 is provided to prevent inadvertent turning of the screw 39.

Attached to the disc 33 is an insulated "pusher" 42 which deflects a pair of gold-plated contact switch wires 43 actuating the electronics. These switch wires offer extremely low pressure-hysteresis between the pressure at which the switch closes and that at which it opens. This is a considerable advantage over an alternative microswitch arrangement.

The "off" switch 43, which is accessible from outside the casing, is axially aligned with the connecting tube 31. Thus, its actuating forces are fairly transmitted to the support structure.

The alarm also includes a battery 44 and an audible alarm device 45 sold under the trade mark "SONAL-ERT".

The electronics of the alarm (FIG. 6) are powered by a manganese-alkaline battery 44 which although having a shorter life than a mercury type offers a more linear discharge voltage and hence a more reliable warning of impending failure.

The pressure switch (S1) operates three circuits. First it charges C1 up to +9 V turning on Q2 and supplying base current to Q1 which turns on power to the rest of the alarm; this is the "alarm-permitting" circuitry. This power will remain available without further closures of S1 for at least 5 minutes at full alarm current, as the drain from C1 is multiplied by Beta of Q2 and Beta of Q1 to represent available circuit current at the collector of Q1.

Closing S2 discharges C1 thereby reducing Q1 collector current to less than 0.5 microamp effectively disabling the alarm.

Switch S2 is normally off and is operated by a spring loaded push button such that after being depressed it automatically returns to the off position.

Once alarming the device will deplete the charge on C1 within 5–10 minutes. The alarm will then cease. This is of no consequence as a paralyzed patient could not survive such a long disconnection.

The pressure switch also drives the C3-R10 differentiator the positive spike from which pulls the cathode of D3 to ground. the Schmitt Trigger inputs are internally protected against the negative spike. If the breathing-rate is greater than 1 Hz this represents a non-physiological condition and hence the differentiators are designed not to produce spikes, thus an alarm will sound. When the cathode of D3 goes down, D3 turns on and C4 is rapidly discharged. When D3 is off C4 slowly charges up through R12 until if no pressure switch closure occurs for approximately 20 seconds, it reaches a sufficient voltage to turn off D4 which has previously been holding C5 discharged. When D4 turns off Schmitt Trigger S.T. 5 begins alternately charging C5 through R15 and discharging it through R14 in parallel with R15 providing an output which is low for 25 ms and high for 250 ms. Buffer S.T. 4 isolates the oscillator from the non-linear load of the "Sonalert Beeper". The resulting pulsating 4 kHz tone alerts attendants that a disconnection has occurred.

The pressure switch has a third function, that of driving the differentiator C2-R8. The positive spike from this network is buffered by S.T. 1, 2 and 3 in parallel and flashes the light-emitting diode informing attendants that a breath has occurred and been detected by the alarm.

If the battery voltage falls to the point where less than 100 hours service remains (V BATT.=6.5 v) the voltage sensing L.E.D. (Hewlett-Packard 5082-4732) and the voltage dropping diodes in series will no longer have sufficient voltage to light the L.E.D. Hence the L.E.D. stops flashing and it becomes apparent that the battery needs replacing. The alarm circuit of course continues to function.

Electrical Characteristics

I "OFF"=0.5 microamps.
I "RUN"=0.5 ma (Average)-Respiratory rate=20 min$^{-1}$
I"ALARM"1.2 ma (Average) 12 ma (Peak)
MAX. "Circuit Fail" Battery Voltage=6.0
MIN. "Batt. Lo Detect" Battery Voltage=6.5

In FIG. 6 all diodes are OA 202 (except the L.E.D.). Schmitt triggers 1-6 are in a single unit sold under the trademark National Semiconductor MM74C914. The L.E.D. is Hewlett Packard H.P. 5082-4732 (Volt Sens). All capacitances are in microfarads and all resistances in ohms.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A ventilator disconnection alarm for monitoring a patient connected to a ventilator, said ventilator disconnection alarm comprising
   warning means for producing an audible warning;
   a source of power;
   a first switch operated by each breath delivered to a patient connected to the ventilator;
   a control circuit including said first switch and connected to said source of power and coupled to said warning means for initiating operation of said warning means when operation of said first switch due to occurrence of a breath of the patient fails to occur at predetermined short intervals of time;
   an actuating circuit connected to said source of power and to said warning means and between said control circuit and said warning means, said actuating circuit being connected to said first switch in a manner whereby operation of said first switch results in said actuating circuit placing said warning means in operable condition by connecting said source of power to said warning means; and
   a second manually-operable switch connected to said actuating circuit for placing said warning means in inoperable condition by disconnecting said source of power from said warning means.

2. A ventilator disconnection alarm as claimed in claim 1, wherein said actuating circuit includes timing means for setting each of the predetermined short intervals of time at approximately 20 seconds.

3. A ventilator disconnection alarm as claimed in claim 1, wherein said source of power constitutes a source of electrical energy, said control and actuating circuits constitute electrical circuits and said first and second switches constitute electric switches.

4. A ventilator disconnection alarm as claimed in claim 3, further comprising visual means electrically connected to said first switch and to said source of electrical energy for visibly indicating the operation of said first switch.

5. A ventilator disconnection alarm as claimed in claim 3, wherein said source of electrical energy is a storage battery.

6. A ventilator disconnection alarm for monitoring a patient connected to a ventilator, said ventilator disconnection alarm comprising
   warning means for producing an audible warning;
   a source of power;
   a first switch operated by each breath delivered to a patient connected to the ventilator;
   a control circuit including said first switch and connected to said source of power and coupled to said warning means for initiating operation of said warning means when operation of said first switch due to occurrence of a breath of the patient fails to occur at predetermined short intervals of time;
   an actuating circuit connected to said source of power and to said warning means and between said control circuit and said warning means, said actuating circuit being connected to said first switch in a manner whereby operation of said first switch results in said actuating circuit placing said warning means in operable condition by closing a circuit between said control circuit and said warning means; and
   a second manually-operable switch connected to said actuating circuit for placing said warning means in inoperable condition by interrupting the circuit between said control circuit and said warning means.

* * * * *